(12) United States Patent
Fernández López et al.

(10) Patent No.: US 11,540,646 B2
(45) Date of Patent: Jan. 3, 2023

(54) METHOD AND SYSTEM FOR IMPROVING QUALITY OF SLEEP AND MATTRESS COMPRISING THE SYSTEM

(71) Applicant: Descansare Sleep Lab, S.L., Logroño (ES)

(72) Inventors: Javier Fernández López, Logroño (ES); Ignacio Gómez Vinagre, Logroño (ES); Oscar Valdemoros Tobia, Logroño (ES)

(73) Assignee: Descansare Sleep Lab, S.L., Logroño (ES)

( * ) Notice: Subject to any disclaimer, the term of this patent is extended or adjusted under 35 U.S.C. 154(b) by 932 days.

(21) Appl. No.: 16/342,406

(22) PCT Filed: Oct. 17, 2017

(86) PCT No.: PCT/ES2017/070685
§ 371 (c)(1),
(2) Date: Apr. 16, 2019

(87) PCT Pub. No.: WO2018/073473
PCT Pub. Date: Apr. 26, 2018

(65) Prior Publication Data
US 2019/0246808 A1    Aug. 15, 2019

(30) Foreign Application Priority Data
Oct. 17, 2016 (ES) ................ ES201631336

(51) Int. Cl.
*A47C 31/12* (2006.01)
*A61B 5/00* (2006.01)
*A47C 21/00* (2006.01)

(52) U.S. Cl.
CPC .......... *A47C 31/123* (2013.01); *A47C 21/003* (2013.01); *A61B 5/4806* (2013.01); *A61B 5/4809* (2013.01); *A61B 5/4815* (2013.01); *A61B 5/6891* (2013.01)

(58) Field of Classification Search
CPC .................................... A47C 31/123
See application file for complete search history.

(56) References Cited

U.S. PATENT DOCUMENTS

| | | | | |
|---|---|---|---|---|
| 2008/0275349 A1* | 11/2008 | Halperin | ........... | A61B 5/447 600/364 |
| 2014/0259434 A1* | 9/2014 | Nunn | ........... | A47C 31/008 5/713 |
| 2015/0164409 A1* | 6/2015 | Benson | ........... | A61B 5/1116 600/595 |
| 2016/0192886 A1 | 7/2016 | Nunn et al. | | |
| 2017/0318981 A1* | 11/2017 | Duwell | ........... | A47C 27/082 |

FOREIGN PATENT DOCUMENTS

| AU | 2016101314 A4 | 8/2016 |
|---|---|---|
| CN | 104732250 A | 6/2015 |
| CN | 105167460 A | 12/2015 |

* cited by examiner

*Primary Examiner* — Joseph H Feild
*Assistant Examiner* — Pameshanand Mahase
(74) *Attorney, Agent, or Firm* — Wiggin and Dana LLP

(57) ABSTRACT

The present invention relates to a method for improving sleep quality, comprising the steps of measuring pressure by means of sensors in locations distributed by regions of a mattress; calculating the SQI based on the prominent movements detected depending on the time of night; calculating the mean pressure measured by each sensor; calculating the difference between the mean pressure and the pressure measured by that sensor when there is no user on the mattress; calculating the mean pressure difference for each region of the mattress; calculating a weight factor for each region of the mattress; comparing the weight factor with a reference value; varying the configuration of the mattress by increasing or reducing the support level in the regions. The present invention also relates to a related system and mattress.

19 Claims, No Drawings

METHOD AND SYSTEM FOR IMPROVING QUALITY OF SLEEP AND MATTRESS COMPRISING THE SYSTEM

TECHNICAL FIELD

The present invention generally relates to the field of mattresses and other resting surfaces, and more particularly to a method for improving sleep quality.

PRIOR ART

Sleep plays a role in most physiological and psychological processes and is in turn affected by them, although it may also be affected by external circumstances, specifically by the mattress.

Sleep is not a process that continues throughout the entire night, rather it consists of a cycle which is repeated several times, and which in turn consists of two main blocks: non-REM (NREM) sleep consisting of four stages, and REM sleep. The NREM-REM cycle starts with the NREM stage that lasts for about 80 minutes, followed by REM sleep that lasts for about 10 minutes. This cycle, with significant individual variation, is repeated 3 to 6 times throughout the night, the amount of NREM sleep decreasing in each cycle and the amount of REM sleep increasing.

Stage IV of NREM sleep is the so-called deep sleep. It is hard to wake up in this stage which takes up 20% of the total sleep time and in which dreams do not usually occur. This is considered to be the stage which determines a good or poor quality sleep, i.e., whether or not the sleep was reinvigorating.

There are several ways in which a mattress can affect the sleep cycle. This may, for example, be the case where one sleeps on a mattress with a support layer that is not optimized for their body shape: a curvature of the backbone will lead to pressure on the spinal nerves in the position in which they come out of the backbone. Another effect caused by the foregoing may include pressure applied on exposed body parts (hips, shoulders, etc.), which can lead to a significant concentration of pressure. Often, thin blood vessels called capillaries are unable to cope with said concentration of pressure and this will be lead to a disturbance in blood flow, and as a result an insufficient oxygen and nutrient supply.

In a situation like this in an unconscious state (i.e., during sleep), the body can only do one thing: to trigger an alarm to wake up. By doing so, the sleep cycle progresses to a higher stage, allowing the person to become aware of what is happening and to react voluntarily using the motor nervous system to turn their body to adopt a better posture which will at least momentarily eliminate the situation generated by the alarm. After this action, sleep will continue towards deeper sleep levels and follow its natural order, at least until other disturbances cause the user to wake up again.

If such disturbance is too intense, or if the physical constitution of the person favors same, the body will react in the manner described above in short intervals, which will affect sleep stages, such as deep sleep, that are usually highly protected against sleep disturbances. When one ages or losses body mass, the body is evidently compelled to use the defense system to wake up even in earlier sleep stages, which negatively affects deep sleep and the significant value it has on health.

It can be assumed that the body protects deep sleep in a special manner, since this is the stage in which the largest amount of growth hormones essential for vital processes in cell renewal functions are secreted. During the deep sleep period, i.e., mainly in the first half of the night, the "threshold for waking up" seems to be significantly greater than later in the night, and therefore interruptions in this first half of the night are obviously more detrimental to sleep than in the last half of the night. A mattress the configuration of which will cause the user to have to move in order to free themselves from situations such as those described where certain parts of their body are subjected to stress, where said movements are prominent enough so as to disturb the sleep cycle, will therefore cause a larger or smaller impact on sleep quality and on the subsequent reinvigorating effect thereof depending on the time of night at which it occurs.

Mattresses having a layer with multiple configurable elements, such as for example, air chambers, water chambers, foam inserts, etc., designed to provide optimum support to the user depending on their anatomy, and to thereby improve sleep quality a priori, are known in the art. These configurable elements are located close to one another in the direction of the cross-section of the mattress and are usually embedded in a foam layer. A layer having multiple regions is thus made, where the other layers of the mattress are made of any other commonly used material, such as foam, springs, latex, etc.

The support level applied by each of the configurable elements can be individually controlled, as disclosed in patent document EP2490575, for example.

The support level can therefore be controlled by means of interchangeable foam inserts, controlling the pressure level of air chambers by means of a pump, controlling the water level in water chambers, etc.

However, there is still a need in the art for a method which allows continuously improving sleep quality night after night by making periodic changes in the configurable elements of the mattress depending not only on the anatomy of the user but also on their sleep quality, and particularly on deep sleep disturbances, until obtaining optimum sleep quality, which is as close as possible to the ideal sleep quality, defined as that in which between 4 and 6 sleep cycles are completed in one night without interruptions.

DISCLOSURE OF THE INVENTION

To solve the problems of the prior art, the present invention discloses a method for improving sleep quality comprising the steps of:
  consistently measuring the pressure applied by the user by means of various sensors controlling various regions of a mattress;
  calculating the sleep quality index (SQI) for at least one night based on the prominent movements (those which disturb sleep cycles) of the user detected by the sensors throughout the night, where a score is assigned to each detected prominent movement depending on the time of night at which it occurs (based on the influence thereof on deep sleep disturbance);
  calculating the weight factor for each region of the mattress comprising the steps of:
    calculating the mean pressure measured by each sensor throughout the night;
    calculating the difference between the mean pressure measured by each sensor and the pressure measured by that sensor when there is no user on the mattress;
    calculating the mean pressure difference for each region of the mattress;
  comparing the weight factor with a reference value;

if the weight factor is greater than the reference value, giving an indication for the support level in that location to be reduced (either by reducing air pressure, changing foam elements for other softer elements, removing water, etc.);

whereas if the weight factor is less than the reference value, giving an indication for the support to be increased;

increasing or reducing the support level in each location depending on the comparison of the weight factor with the reference value.

The steps of the described method are periodically repeated until obtaining the optimum SQI value.

According to another aspect, the present invention discloses a system for improving sleep quality comprising a plurality of pressure sensors controlling various regions of a mattress, a programmed control unit which can preferably be connected via the Internet to a remote unit to perform the steps of the method according to the present invention, input means for a user to enter data into the control unit, and output means for providing sleep quality results to the user.

According to an additional aspect, the present invention also discloses a mattress divided into regions, where each region is divided into locations, in which the pressure in each of the locations can be varied independently of the other locations, characterized in that it comprises a system according to the present invention.

This thereby allows obtaining a continuous improvement of sleep quality night after night until obtaining optimum sleep quality.

DETAILED DISCLOSURE OF THE INVENTION

As mentioned above, the preferred embodiment of the present invention discloses a method for improving sleep quality comprising the steps of:

consistently measuring the pressure by means of various sensors controlling various regions of a mattress, where said sensors can be located in several regions of the mattress or in an external control unit, for example, but connected to each monitored region;

calculating the sleep quality index (SQI) for at least one night based on the prominent movements of the user detected by the sensors throughout the night, where a score is assigned to each detected prominent movement depending on the time of night at which it occurs;

calculating the weight factor for each region of the mattress comprising the steps of:

calculating the mean pressure measured by each sensor throughout the night;

calculating the difference between the mean pressure measured by each sensor and the pressure measured by that sensor when there is no user on the mattress;

calculating the mean pressure difference for each region of the mattress;

comparing the weight factor with a reference value;

if the weight factor is greater than the reference value, giving an indication for the support level in that location to be reduced; whereas if the weight factor is less than the reference value, giving an indication for the support to be increased;

increasing or reducing the support level in each location depending on the comparison of the weight factor with the reference value.

The steps of the method according to the present invention are periodically repeated until obtaining the optimum SQI value.

According to one embodiment of the present invention, the user starts the pressure measurement right before getting into bed. According to another embodiment, the pressure measurement can be programmed so that it starts at a later time, assuming that the user does not sleep right after getting into bed and that prominent movements may therefore occur before the user is actually asleep.

According to the preferred embodiment of the invention, the method comprises the prior step of detecting the start of sleep, defined as the initial instant of the first 30 minutes of the night in which no movement whatsoever occurs. In this case, it is understood that if the user does not move for 30 minutes, then the user has fallen asleep. The initial point of sleep is therefore minute 0 of that first 30-minute period in which no movement whatsoever occurs.

The sleep quality index (SQI) is the parameter indicating the actual sleep quality of the user. To calculate such index, the mattress, through its control unit and pressure sensors, must run a permanent pressure mapping method throughout the entire night. The sleep quality index is calculated based on all the prominent movements throughout the entire night, since these prominent movements are assumed to cause disturbances in the sleep cycle.

Furthermore, a different score will be assigned to each of these prominent movements depending on the time of night at in which they occur, where prominent movements that occur in the first part of the night (deep sleep) are more detrimental.

According to a preferred embodiment of the present invention, prominent movements are those which cause a change in pressure of more than 3 mbar on a surface of the mattress corresponding to at least 30% of the total area covered by the user's torso, the torso being understood as the part of the body going from the shoulders to the hip. A change in pressure of more than 3 mbar must be understood as a cumulated variation where it is the result of the changes in pressure measured simultaneously in all the sensors encompassing said surface. Preferably, said change in pressure is between 6 and 8 mbar, and the sensors that must detect the changes in pressure are 3 in number. According to another preferred embodiment, the change in pressure is between 4 and 6 mbar, and the sensors that must detect the changes in pressure are 2 in number. The person skilled in the art will understand that the number of sensors can be different depending on the technical features of the mattress.

The sleep quality index is divided into 10 levels (on a scale of 1 to 10:1 corresponds to the best result and 10 to the worst result). The person skilled in the art will understand that it is a calculation example, where other numerical reference values can be applied. The sleep quality index is related to the number of prominent movements and the time at which they occur. If these movements occur in the early sleep stage (deep sleep), they will negatively affect sleep quality. Therefore, as described different scores are assigned to these movements depending on the sleep stage.

The SQI is then calculated as the sum of the scores of all the prominent movements detected throughout the night divided by the minutes of sleep and multiplied by 60.

The following table shows an exemplary assignment of scores which can be used depending on the hour of sleep at which the prominent movements occur:

$1^{st}$ hour: 10 points
$2^{nd}$ hour: 10 points
$3^{rd}$ hour: 8 points

4$^{th}$ hour: 8 points
5$^{th}$ hour: 5 points
6$^{th}$ hour: 4 points
7$^{th}$ hour: 2 points
8$^{th}$ hour: 1 points Therefore, if a case of a 7.5-hours sleep (which is considered a sufficient sleep duration for an adult to have proper rest) is considered, for example, in which a prominent movement is detected in every hour of sleep and two movements in the 6$^{th}$ hour, the following total score for the prominent movements will be obtained:

10+10+8+8+5+4+4+2+1=52

The SQI can then be calculated as described above:

SQI=52/450*60=6.93

As can be seen, this value is far from the optimum SQI value (a value of 1 according to the given example), modifications must therefore be made to improve sleep quality for the next night.

SQI calculation is preferably repeated for three consecutive nights. The mean value which most accurately reflects sleep quality is thus obtained.

The variation of the support level that must be applied in each location of the mattress is then thereby determined.

The mattress is divided into 3 main regions: shoulders, waist and hip. Each of those regions comprises several locations in which configurable elements as mentioned above, in addition to associated pressure sensors, are located.

By way of example, a mattress having 12 air ducts the pressure of which can be varied is considered, where each duct is associated with a pressure sensor. Ducts 1-3 correspond to the shoulders, ducts 4-5 to the waist and ducts 6-10 to the hip. The following table shows exemplary pressure readings obtained throughout a night with a mattress of this type:

fifth column shows the three regions into which the mattress is divided, as mentioned above (1: shoulders, 2: waist, 3: hip).

The mean pressure difference for each region of the mattress is then calculated (column 6).

According to the preferred embodiment of the present invention, the weight factor (column 7) is calculated by dividing the mean pressure difference for each region by the user's BMI (body mass index, in this case 22.04) and multiplying the result by 10.

The calculated weight factor is then compared with a reference value (column 8 for men and column 9 for women). The reference values are empirically obtained optimum values.

Finally, the type of variation of the support that must be performed in various locations of the mattress is determined. If the weight factor is greater than the reference value, an indication to reduce the air pressure in that location is given; whereas if the weight factor is less than the reference value, an indication to increase the pressure is given.

According to a preferred embodiment of the present invention, the method comprises not only giving an indication of the variation in pressure that must be applied in each location of the mattress (for example, so that a user can perform said change manually), but also comprises automatically increasing or reducing the pressure in each location depending on the comparison of the weight factor with the reference value.

For example, this automatic variation can be done by means of an air pump in the case of a mattress comprising air chambers as configurable pressure elements.

The SQI is then measured again according to the steps described above for at least one night (preferably 3). If the value that is obtained is better than the preceding value (according to the established calculation system, in the case of the example provided in the present description, the value is closest to the ideal value of 1), an improvement in sleep quality is obtained. The objective of the invention is to keep repeating the steps of the method periodically until obtaining

| Air ducts | Pressures in the ducts (mbar) | Mean pressures measured in each duct (mbar) | Pressure difference (mbar) | Region | Mean pressure difference | Weight factor | BMI = 22.04 | |
|---|---|---|---|---|---|---|---|---|
| | | | | | | | Reference value Men | Reference value Women |
| 1 | −7.5 | 4 | 11.5 | 1 | 12.67 | 5.7 | 5 | 6 |
| 2 | −7.5 | 5 | 12.5 | 1 | | | | |
| 3 | −4 | 10 | 14 | 1 | | | | |
| 4 | 1 | 15 | 14 | 2 | 13 | 5.9 | 6 | 6 |
| 5 | 20 | 32 | 12 | 2 | | | | |
| 6 | 1 | 16 | 15 | 3 | 12.6 | 5.7 | 6 | 5 |
| 7 | −4 | 10 | 14 | 3 | | | | |
| 8 | −4 | 9 | 13 | 3 | | | | |
| 9 | 1 | 12 | 11 | 3 | | | | |
| 10 | 1 | 11 | 10 | 3 | | | | |
| 11 | 1 | 11 | 10 | | | | | |
| 12 | 1 | 10 | 9 | | | | | |

In this sense, the second column represents the pressure measured by each sensor when there is no user on the mattress (a mattress the regions of which have been previously configured using techniques known in the prior art of mattresses customized depending on sex, weight, height, etc.), whereas the third column represents the mean pressure measured by each sensor throughout the night. The difference between both values is shown in the fourth column. The the optimum value (in the case of the calculation applied in the example of the present invention, the optimum value is the value closest to 1) which would mean that a given user has achieved optimum sleep quality, i.e., quality that is the closest to the one without arousals that cause sleep interruptions.

Another aspect of the present invention discloses a system for putting the method described above into practice. To that end, the system for improving sleep quality comprises a plurality of pressure sensors controlling various regions of a mattress, a programmed control unit which can preferably be connected via the Internet to a remote unit to perform the steps of the method as described herein above, input means for a user to enter data into the control unit, and output means for providing sleep quality results to the user.

According to one embodiment of the invention, the sensors, the control unit and the input and output means are all connected by a cable, said input means and output means being implemented by means of a user interface incorporated in the mattress.

For example, the user interface can be located on one side of the mattress and can be a touch screen, a combination of a screen and buttons, etc. The user enters data such as height, weight, etc. The user can also enter the desired initial pressure values if the system allows automatically varying the pressure in each of the locations of the mattress.

According to another preferred embodiment, the input means and the output means are implemented by means of a computer program or application that the user can install in a device belonging to the user, such as a computer, tablet, smartphone, etc. In this case, the control unit wirelessly communicates with the user device. The program or application installed in the user device is also envisaged to be able to carry out the method described above, said user device thereby acting as a control unit. In this case, the only element that is physically implemented in the mattress is the pressure sensors which communicate with the user device by wireless means.

As mentioned above, according to the preferred embodiment of the present invention the system further comprises means for varying the pressure in various locations of the mattress, such as an air pump connected to various air chambers distributed in the locations of the mattress, for example.

Finally, the present invention also discloses a mattress divided into regions, where each region is divided into locations, in which the pressure in each of the locations can be varied independently of the other locations, as described herein above. The mattress of the invention further comprises a system as described above.

The present invention therefore offers a method and a system which allow improving sleep quality night after night by making periodic changes in the configurable elements of the mattress depending not only on the anatomy of the user but also on sleep quality, and particularly on sleep disturbances, especially in the deep sleep stage, that are caused by prominent movements, until obtaining an optimum sleep quality, i.e., one which is as close as possible to the ideal sleep quality, defined as that in which between 4 and 6 cycles of sleep are completed in one night without interruptions. So the method and system according to the present invention will continue to propose changes in the configuration of the mattress as long as improvements in sleep quality can be attained, all this depending on each particular user.

Although the present invention has been described above in reference to a specific embodiment thereof, modifications and variations of said embodiment may occur to the person skilled in the art without departing from the scope of the present invention. For example, the person skilled in the art may change the number of locations, regions, locations per region, etc. of the mattress in order to put the method of the invention into practice. Furthermore, the variation of the support level in said locations is not limited to varying the air pressure in an air chamber, rather it may consist of varying the water level in a water chamber, varying the consistency/number of foam inserts incorporated in each location, etc.

The invention claimed is:

1. A method for improving sleep quality, which comprises consistently measuring the pressure applied by a user by means of various sensors controlling various regions of a mattress, the method comprising the steps of:
    calculating the sleep quality index (SQI) for at least one night based on prominent movements of the user detected by the sensors throughout the night, wherein prominent movements are those which cause a change in pressure of more than 3 mbar on a surface of the mattress corresponding to at least 30% of the total area covered by the user's torso, and wherein a score is assigned to each detected prominent movement depending on the time of night at which it occurs;
    calculating the weight factor for each region of the mattress comprising the steps of:
        calculating the mean pressure measured by each sensor throughout the night;
        calculating the difference between the mean pressure measured by each sensor and the pressure measured by that sensor when there is no user on the mattress; and
        calculating the mean pressure difference for each region of the mattress;
    comparing the weight factor with a reference value;
    if the weight factor is greater than the reference value, giving an indication for the support level in that location to be reduced; whereas if the weight factor is less than the reference value, giving an indication for the support level to be increased; and
    increasing or reducing the support level in each location depending on the comparison of the weight factor with the reference value.

2. The method according to claim 1, characterized in that the sleep quality index (SQI) for three consecutive nights is calculated.

3. The method according to claim 2, characterized in that the steps thereof are periodically repeated.

4. The method according to claim 2, characterized in that it comprises the prior step of detecting the start of sleep, defined as the first 30 minutes of the night in which no movement whatsoever occurs.

5. The method according to claim 1, characterized in that said change in pressure is a cumulated variation of changes in pressure measured simultaneously in all the sensors encompassing said surface.

6. The method according to claim 5, characterized in that said change in pressure is between 6 and 8 mbar, and the sensors are 3 in number.

7. The method according to claim 5, characterized in that said change in pressure is between 4 and 6 mbar, and the sensors are 2 in number.

8. The method according to claim 1, characterized in that said change in pressure is between 6 and 8 mbar, and the sensors are 3 in number.

9. The method according to claim 1, characterized in that said change in pressure is between 4 and 6 mbar, and the sensors are 2 in number.

10. The method according to claim 1, characterized in that the SQI is equal to the sum of the scores of all the detected prominent movements divided by the minutes of sleep and multiplied by 60.

11. The method according to claim 1, characterized in that it comprises the prior step of detecting the start of sleep, defined as the first 30 minutes of the night in which no movement whatsoever occurs.

12. The method according to claim 1, characterized in that the step of calculating the weight factor comprises dividing the mean pressure difference for each region by the user's BMI and multiplying by 10.

13. The method according to claim 1, characterized in that the SQI is equal to the sum of the scores of all the detected prominent movements divided by the minutes of sleep and multiplied by 60.

14. A system for improving sleep quality, comprising:
- a plurality of pressure sensors controlling various regions of a mattress;
- a control unit programmed to perform the steps of the method according to claim 1;
- input means for a user to enter data into the control unit; and
- output means for providing sleep quality results to the user.

15. The system according to claim 14, characterized in that the input means and the output means are implemented by means of a user interface incorporated in the mattress.

16. The system according to claim 14, characterized in that the input means and the output means are implemented by means of a computer program in a user device.

17. The system according to claim 14, characterized in that the programmed control unit can be connected via the Internet to a remote unit.

18. The system according to claim 14, characterized in that it further comprises variation means for varying the support level in various locations of the mattress.

19. A mattress divided into regions, where each region is divided into locations, in which the support level in each of the locations can be varied independently of the other locations, characterized in that it comprises a system according to claim 14.

* * * * *